(12) United States Patent
Doyle, III et al.

(10) Patent No.: US 10,507,284 B2
(45) Date of Patent: Dec. 17, 2019

(54) DAILY PERIODIC TARGET-ZONE MODULATION IN THE MODEL PREDICTIVE CONTROL PROBLEM FOR ARTIFICIAL PANCREAS FOR TYPE I DIABETES APPLICATIONS

(71) Applicant: The Regents of the University of California, Oakland, CA (US)

(72) Inventors: Francis J. Doyle, III, Santa Barbara, CA (US); Eyal Dassau, Goleta, CA (US); Ravi L. Gondhalekar, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 951 days.

(21) Appl. No.: 14/154,241

(22) Filed: Jan. 14, 2014

(65) Prior Publication Data

US 2014/0200559 A1     Jul. 17, 2014

Related U.S. Application Data

(60) Provisional application No. 61/751,942, filed on Jan. 14, 2013.

(51) Int. Cl.
| | | |
|---|---|---|
| *A61M 5/172* | (2006.01) | |
| *A61M 5/142* | (2006.01) | |
| *G16H 50/50* | (2018.01) | |
| *G06F 19/00* | (2018.01) | |

(52) U.S. Cl.
CPC ...... *A61M 5/1723* (2013.01); *A61M 5/14276* (2013.01); *G06F 19/3456* (2013.01); *G16H 50/50* (2018.01)

(58) Field of Classification Search
CPC ............. G06F 19/3468; G06F 19/3437; G06F 19/3456; G06F 19/345; A61M 5/1723; A61M 5/14532; A61M 2005/14208
See application file for complete search history.

(56) References Cited

U.S. PATENT DOCUMENTS

| | | | |
|---|---|---|---|
| 9,486,578 B2* | 11/2016 | Finan | A61M 5/1723 |
| 2008/0097289 A1* | 4/2008 | Steil | A61M 5/1723 604/67 |
| 2010/0145262 A1* | 6/2010 | Bengtsson | A61B 5/14532 604/66 |
| 2011/0106049 A1 | 5/2011 | Diamano | |

* cited by examiner

*Primary Examiner* — Matthew F Desanto
(74) *Attorney, Agent, or Firm* — Richard Aron Osman (57) ABSTRACT

A controller for an artificial pancreas for automated insulin delivery to patients with type 1 diabetes mellitus (T1DM) that enforces safe insulin delivery throughout both day and night, wherein the controller employs zone model predictive control, whereby real-time optimization, based on a model of a human's insulin response, is utilized to regulate blood glucose levels to a safe zone, and time-dependent zones that smoothly modulate the controller correction based on the time of day, wherein the controller strategically strives to maintain an 80-140 mg/dL glucose zone during the day, a 110-220 mg/dL zone at night, and a smooth transition of 2 hour duration in between.

9 Claims, 7 Drawing Sheets

DAILY PERIODIC TARGET-ZONE MODULATION IN THE MODEL PREDICTIVE CONTROL PROBLEM FOR ARTIFICIAL PANCREAS FOR TYPE I DIABETES APPLICATIONS

This application claims priority to Ser. No. 61/751,942, filed Jan. 14, 2013, having the same title and inventors.

This invention was made with government support under Grant Numbers DP3DK094331 and ROIDK085628 awarded by the National Institutes of Health (NIH). The government has certain rights in the invention.

INTRODUCTION

Type 1 Diabetes Mellitus (T1DM) is a metabolic autoimmune disease characterized by the destruction of the pancreas' beta cells, and results in the body being incapable of producing insulin, a hormone that serves at least two important functions. The first is to facilitate the absorption of glucose from the blood-stream into many types of cell. The second function is to participate, in conjunction with glucagon (insulin's antagonist), in the endocrine feedback loop that regulates the liver's release/removal of glucose into/from the blood-stream. Thus people with T1DM first require the delivery of insulin into their blood-stream from an external source in order to fuel their cells, and second tend to suffer great difficulty maintaining healthy blood-glucose levels. Hypoglycemia has very near-term consequences and may result in, e.g., dizziness or disorientation if mild, fits or unconsciousness if serious, and irreversible coma or death in severe cases. In contrast, a hyperglycemic state has few consequences if it is brief. However, a blood-glucose level that is high on average over long periods of time may result in a plethora of health problems, e.g., cardiovascular disease, kidney failure and retinal damage, possibly many years down the line.

The overall goal of this work is an artificial pancreas for the automated delivery of insulin to people with T1DM [1, 2, 3]. A crucial element of any fully automated artificial pancreas is a feedback control law that performs algorithmic insulin dosing that is effective and safe. A variety of such glycemia controllers have been proposed, e.g., based on Model Predictive Control (MPC) [4, 5, 6, 7], proportional-integral-derivative control [8,9], and adaptive neural networks [10]. One advantage of MPC is the large degree of flexibility in formulating the control objective, and this flexibility was exploited in our development of glycemia controllers based on zone-MPC [5, 6, 11], whereby the blood-glucose levels are controlled with respect to the inclusion within a safety-set, rather than to track a singular set-point. The reason this has proven effective in real-life operation of the controller is twofold. First, there is generally a significant plant-model mismatch due to the large inter- and intra-subject variability of humans' physiology. Second is that the feedback signals, an estimate of the blood-glucose level provided every 5 minutes by a continuous glucose monitor [12], suffers large errors and delays, both of which have time-varying properties and have proven difficult to model and correct for. The use of zone-MPC provides robustness against excessively responding to noise in the state estimate when the blood-glucose level is estimated to be within the safe zone. The work presented here is an innovative extension of the zone-MPC strategy presented in [5, 6, 11].

Rigorous testing of an artificial pancreas requires, first, operation of the controller for prolonged, all-day and multiday periods of time, and, second, to move trials from the clinic to an outpatient environment. A major concern is a nocturnal hypoglycemic event, and the motivation for this paper is to tackle this issue. While the subject is awake it is desirable to keep blood-glucose levels towards the lower end of the safe range, at the risk of a higher probability of experiencing a hypoglycemic event. The assumption is that the subject either will become aware of her/his state, or be made aware of it by a hypoglycemia alarm system, and correct appropriately. However, if subjects fail to notice their state or to perceive alarms, and therefore do not enforce corrective action, then the controller must strive to reduce the risk of hypoglycemia. The invention provides a zone-MPC law that strategically reduces the risk of hypoglycemia during the night—assumed to be the time of sleep. One innovation over the time-invariant zone-MPC strategy of [5, 6, 11] is that the invention is periodically time dependent w.r.t. the time of day. Specifically, during the night the blood-glucose target zone is raised, and the bound on the maximum insulin infusion rate is reduced, from the values employed during the day. The motivation for the former is to induce a rise of blood-glucose levels at night. The latter is enforced as a further safety mechanism and reduces the chance of controller induced hypoglycemia.

SUMMARY OF THE INVENTION

The key component in a successful artificial pancreas system designed to maintain the blood glucose concentrations of people with type 1 diabetes mellitus within the euglycemic zone (80-140 mg/dL) is the control algorithm, which automatically directs the delivery of insulin to be administered to a subject with type 1 diabetes. The controller must meet a variety of challenges, such as the inherent long time delays between subcutaneous sensing, subcutaneous pump action, and the body's insulin-blood glucose dynamics, among others. Our artificial pancreas research group has designed and tested controllers that meet these challenges. However, clinical tests are limited in scope and length due to the risks of hypoglycemia during times of patient sleep. The present invention facilitates the testing and verification of glycemia controllers over prolonged, multi-day periods of time. The disclosed controllers achieve this safely by continuously modulating their control objective depending on the time of day. Specifically, the target blood glucose zone values during the night are higher than during the day, and there is a period of smooth transition between the daytime and nighttime. Furthermore, the insulin input constraints enforced by the controller are lower during the night than during the day. These characteristics permit elevated blood glucose levels during the night, and reduce the maximum amount of insulin deliverable by the artificial pancreas device while the patient is asleep. The risk of (controller induced) hypoglycemia during periods of sleep is thus reduced.

In one aspect the invention provides a controller for an artificial pancreas for automated insulin delivery to patients with type 1 diabetes mellitus (T1DM) that enforces safe insulin delivery throughout both day and night, wherein the controller employs zone model predictive control, whereby real-time optimization, based on a model of a human's insulin response, is utilized to regulate blood glucose levels to a safe zone, and time-dependent zones that smoothly modulate the controller correction based on the time of day, wherein the controller strategically strives to maintain an 80-140 mg/dL glucose zone during the day, a 110-220 mg/dL zone at night, and a smooth transition of 2 hour duration in between.

In another aspect the invention provides a controller for an artificial pancreas that automatically directs the delivery of insulin to maintain blood glucose concentrations of people with type 1 diabetes mellitus (T1DM) within the euglycemic zone (80-140 mg/dL) using a control algorithm that continuously modulates the control objective depending on the time of day, wherein target blood glucose zone values during the night are higher than during the day, there is a period of smooth transition between the daytime and nighttime, and insulin input constraints enforced by the controller are lower during the night than during the day, wherein elevated blood glucose levels are permitted during the night, and the maximum amount of insulin deliverable by the artificial pancreas device while the patient is asleep is reduced, and risk of controller induced hypoglycemia during periods of sleep is thus reduced.

In another aspect the invention provides a periodic zone model predictive control (PZMPC) controller adapted for directing insulin, particularly from an artificial pancreas.

The invention also provides corresponding algorithms for programming the subject controllers to effectively implement the disclosed control steps.

The invention also provides an artificial pancreas system or subsystem comprising a subject controller, which may comprise for example, the controller and a pump (e.g. subcutaneous).

The invention also provides a periodic zone model predictive control (PZMPC) scheme of an artificial pancreas (AP) for Type 1 diabetes applications comprising a control algorithm which directs a subject controller.

The invention also provides a method comprising directing and optionally, delivering, insulin delivery using a subject controller.

The invention includes controllers, algorithms and insulin directing systems essentially as described herein, and all combinations of the recited particular embodiments. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

DESCRIPTION OF PARTICULAR EMBODIMENTS OF THE INVENTION

The invention provides an artificial pancreas for automated insulin delivery to patients with type 1 diabetes mellitus (T1DM). A crucial element of any fully automated artificial pancreas is a strategy to perform safe and effective insulin dosing, and we have successfully developed control algorithms that achieve this task. Rigorous testing requires first to operate controllers for multi-day periods, and second to move trials from clinics to an outpatient environment. The invention provides a fully automatic control strategy that enforces safe insulin delivery throughout both day and night.

The control strategy employs zone model predictive control, whereby real-time optimization, based on a model of a human's insulin response, is utilized to regulate blood glucose levels to a safe zone. One inventive aspect of our solution is the use of time-dependent zones that smoothly modulate the controller correction based on the time of day. Specifically, the controller strategically strives to maintain an 80-140 mg/dL glucose zone during the day, a 110-220 mg/dL zone at night, and a smooth transition of 2 hour duration in between.

Based on a test of 10 in silico adult subjects on a typical meal schedule, the subject controller administers on average 7.0% and 2.2% less insulin during the night than current fixed-zone controllers and basal-bolus therapy, respectively, and thereby alleviates the risk of nocturnal hypoglycemia. Furthermore, the controller produces excellent responses to unannounced meals, severe hyperglycemia and unannounced, self-administered insulin boluses.

The subject control strategy is a significant step towards safe and continuous evaluation of artificial pancreases on people with T1DM in an outpatient environment for prolonged periods of time.

II. PERIODIC-ZONE MPC STRATEGY

In this section the disclosed Periodic-Zone Model Predictive Control (PZMPC) strategy is described in general engineering terms. The set of real numbers is denoted by $\mathbb{R}$ ($\mathbb{R}_+$ strictly positive), the set of non-negative integers by $\mathbb{N}$ ($\mathbb{N}_+ := \mathbb{N} \setminus \{0\}$), and the set of consecutive non-negative integers $\{j, \ldots, k\}$ by $\mathbb{N}_j^k$.

A. Problem Setting

We consider the discrete-time linear time-invariant (LTI) plant model $$x_{i+1} = Ax_i + Bu_i$$

$$y_i = Cx_i \quad \text{(1a),(1b)}$$

with discrete time-step index $i \in \mathbb{N}$, state $x \in \mathbb{R}^n$, input $u \in \mathbb{R}$, and output $y \in \mathbb{R}$. The disclosed PZMPC strategy is straightforwardly applicable to systems with non-scalar inputs and outputs. We restrict the presentation to single-input single-output (SISO) systems, first for clarity of exposition, second because the insulin-glucose models employed in Sections III and IV are SISO systems.

The control input u is required to satisfy $$\bar{u}_i \leq u_i \leq \hat{u}_i \quad (2)$$

where $\bar{u}, \hat{u} \in \mathbb{R}$ denote time-dependent lower- and upper-bounds, respectively. The bounds $\bar{u}_i, \hat{u}_i$ are assumed known for all $i \in \mathbb{N}$. Eq. (2) is considered a hard constraint here.

It is desired that the output y satisfy $$\bar{y}_i \leq y_i \leq \hat{y}_i \quad (3)$$

where $\bar{y}, \hat{y} \in \mathbf{R}$ denote time-dependent lower- and upper-bounds of the output target-zone, respectively. The bounds $\bar{y}_i, \hat{y}_i$ are assumed known for all $i \in \mathbf{N}$. The output objective (3) is not employed as a hard constraint here; instead, it is treated as a soft constraint by appropriate cost penalization.

Let $p \in \mathbf{N}_+$ denote a finite period length (i.e., corresponding to 24 h for diurnal periodicity).

Assumption 1: For all $i \in \mathbf{N}$ the following holds:

$$\bar{u}_i = \bar{u}_{i+p}, \hat{u}_i = \hat{u}_{i+p},$$

$$\bar{y}_i = \bar{y}_{i+p}, \hat{y}_i = \hat{y}_{i+p},$$

Assumptions 1 has no mathematical consequences here. It is made first because this is the case considered in the application of Sections III and IV, and second because it is the reason for naming the disclosed method Periodic-Zone MPC—it is not a more general periodic MPC strategy that happens to employ zones, like, e.g., [13].

B. Periodic-Zone MPC Problem

For all $i \in \mathbf{N}$ let the zone-excursion be denoted by $$z_i := Z(y_i, \bar{y}_i, \hat{y}_i)$$

with zone-excursion function $Z: \mathbf{R} \times \mathbf{R} \times \mathbf{R} \to \mathbf{R}$:

$$Z(y, \bar{y}, \hat{y}) := \begin{cases} y - \hat{y} & \text{if } y > \hat{y} \\ -y + \bar{y} & \text{if } y < \bar{y} \\ 0 & \text{otherwise.} \end{cases}$$

We denote the prediction horizon by $P \in \mathbf{N}_+$, the control horizon by $N \in \mathbf{N}_1^P$, and two weighting factors for the input u and zone-excursion z by R, $Q \in \mathbf{R}_+$, respectively. The parameters N, P, R and Q are design parameters and assumed to be given (see Section III-D). The PZMPC strategy performs closed-loop control action of the plant by applying at each time step i the first control input of the predicted optimal control input trajectory given by the solution of Problem 2.

Problem 2: Determine $$u_0^*, \ldots, u_{N-1}^* := \underset{\{u_0, \ldots, u_{N-1}\}}{\operatorname{argmin}} \sum_{k=1}^{P} \|z_k\|_Q^2 + \sum_{k=0}^{N-1} \|u_k\|_R^2 \quad (4)$$

subject to $$x_0 := x_i$$

$$x_{k+1} := A x_k + B u_k \forall k \in \mathbf{N}_0^{P-1}$$

$$y_k := C x_k \forall k \in \mathbf{N}_0^P$$

$$u_k := 0 \forall k \in \mathbf{N}_N^{P-1}$$

$$z_k := Z(y_k, \bar{y}_{i+k}, \hat{y}_{i+k}) \forall k \in \mathbf{N}_0^P$$

$$\bar{u}_{i+k} \leq u_k \leq \hat{u}_{i+k} \forall k \in \mathbf{N}_0^{N-1}. \quad (5),(6)$$

The PZMPC state-feedback control law is denoted by $$X(x_i) := u_0^*(x_i).$$

Note that Problem 2 can be formulated as a quadratic program that is convex, although generally not strictly convex.

C. State-Estimator

A state-estimate is required to initialization the predicted state trajectory in (4). A Luenberger-observer is employed (see, e.g., [14]). The state-estimator is based on the same plant model (1) employed for prediction in Problem 2 and is implemented as $$x_i = (I_n - LC)(A x_{i-1} + B u_{i-1}) + L y_i$$

$$L := (R + CPC^T)^{-1} CPA^\bullet$$

$$P = Q + APA^T - APC^T (R + CPC^T)^{-1} CPA^\bullet$$

where $y \in \mathbf{R}$ denotes the measured plant output, and weighting matrices $Q \in \mathbf{R}^{n \times n}$, $Q > 0$ and $R \in \mathbf{R}_+$ are design parameters and assumed to be given (see Section III-D).

III. APPLICATION TO BLOOD-GLUCOSE REGULATION

In this section the details of the model and control objective specific to blood-glucose regulation are introduced. The following units are employed: Deciliters (dL), grams (g), milligrams (mg), hours (h), minutes (min), and units of insulin (U).

A. SISO LTI Model of Eq. (1)

The SISO LTI model of [5] is employed, summarized as follows. The scalar plant input is the administered insulin rate $u_{IN}$ [U/h], and the scalar plant output is the subject's blood-glucose value $y_{BG}$ [mg/dL]. The plant is linearized around a (fictitious) steady-state, that is assumed to be achieved by applying the (subject-specific) basal input rate $u_{basal}$ [U/h], and is assumed to results in a steady-state blood-glucose output $y_{SS} := 110$ [mg/dL]. Let the scalar input and output of LTI model (1) be defined respectively as:

$$u := u_{IN} - u_{basal}$$

$$y := y_{BG} - y_{SS}.$$

The model is a discrete-time system with $T_s = 5$ [min] sample-period. Let $Z^{-1}$ denote the backwards shift operator. The transfer characteristics from u to y are described by $$\frac{Y(Z)}{U(Z)} = \frac{1800 \, Fc}{u_{TDI}} \cdot \frac{Z^{-3}}{(1 - p_1 Z^{-1})(1 - p_2 Z^{-1})^2}$$

with poles $p_1 = 0.98$ and $p_2 = 0.965$, a so-called safety-factor $F := 1.5$ (unitless) (this can be tuned to the subject, but is fixed to 1.5 in this example), the (subject-specific) total daily insulin amount $u_{TDI} \in \mathbf{R}_+$ [U], and where the scalar constant $$c := -0.05(1 - p_1)(1 - p_2)^2 \left[\frac{\text{mg} \cdot h}{\text{dL}}\right]$$

is employed to set the correct gain and for unit conversion. The state-space representation is then (1) with $n = 3$ and $$A = \begin{bmatrix} p_1 + 2p_2 & -2p_1 p_2 - p_2^2 & p_1 p_2^2 \\ 1 & 0 & 0 \\ 0 & 1 & 0 \end{bmatrix}$$

-continued $$B = [1\ 0\ 0]^*$$

$$C = \frac{1800\, Fc}{u_{TDI}}[0\ 0\ 1].$$

B. Periodic Daily Blood-Glucose Target Zone

The main novelty and contribution of the disclosed MPC strategy over [5, 6, 11], w.r.t. glycemia control, is the use of periodically time-dependent output target zones via (3). During the day, the zones are selected equal to those employed in [5, 6, 11]; $\bar{y}$=80 [mg/dL], $\hat{y}$=140 [mg/dL]. This choice provides a good combination of the controller striving to maintain a blood-glucose level that is healthy semi-permanently, while not excessively responding to disturbances and sensor errors with a non-basal insulin delivery.

During the night the following bounds are selected: $\bar{y}$=110 [mg/dL], $\hat{y}$=220 [mg/dL] (see Section III-D). Thus the target zone is both elevated and wider during the night than during the day. The elevated lower bound implies that the controller reduces the insulin input rate to below the basal rate at higher blood-glucose values during the night than during the day. The highly elevated upper bound implies that the controller administers an insulin input rate exceeding the basal rate only at blood-glucose levels that are high enough to pose a serious and near-term health risk. It furthermore implies that during the night the controller makes no attempt to lower any blood-glucose level less than 220 [mg/dL], even though a level of 220 [mg/dL] would pose a considerable health risk if maintained indefinitely. This trade-off appears, at present, to be necessary in order to reduce the likelihood of immediately life-threatening nocturnal hypoglycemic events.

The daytime zone is employed from 7 am to 10 pm, the nighttime zone from 12 pm to 5 am, and there are two two-hour periods in between where the controller smoothly transitions the target zone bounds based on a cosine function. The target zone bounds are plotted over the course of one day in FIG. 1. The transition function is omitted as straightforward.

C. Periodic Daily Insulin Input Constraints

As a further safeguard against insulin overdosing during sleep the disclosed MPC strategy enforces daily periodically time-dependent, hard, insulin input rate constraints via (2).

During daytime the input rate is bounded from above only by the pump's maximum achievable flow-rate, and is thus hardware dependent. Note that this maximum rate is unlikely to ever be commanded by the controller. During nighttime the input rate is limited from above to 1.5× the subject's basal rate (see Section III-D), and is subject-specific. The insulin input rate's lower bound is zero at all times. Daytime is from 5 am to 10 pm. All other times are nighttime—there is no transition period. Note that the start of day- and nighttimes coincides with the start of the output zones' transition periods. The insulin bounds are plotted over the course of one day in FIG. 2.

With sample-period $T_s$=5 [min] the periodic bounds are defined by sequences $\{\bar{y}_j\}_{j=0}^{p-1}$, $\{\hat{y}_j\}_{j=0}^{p-1}$, $\{\bar{u}_j\}_{j=0}^{p-1}$, and $\{\hat{u}_j\}_{j=0}^{p-1}$ of period length p=24 h/$T_s$288. Note that they are defined until shortly before 11 pm, and a very similar output response after about 9 am (next day). All three control strategies produce the same input response until shortly prior to 10 pm, and a very similar input response after 8 am (next day). Note that the PZMPC strategy delivers more insulin in response to the 7 am breakfast than the other two strategies. Some statistics are tabulated in Table I. To summarize, the PZMPC, invariant-zone MPC and nighttime-basal strategies are ordered here according to increasing insulin delivery, and decreasing average blood-glucose levels, both for the whole day and only nighttime.

C. 100 in Silico Subjects

Figure 5:
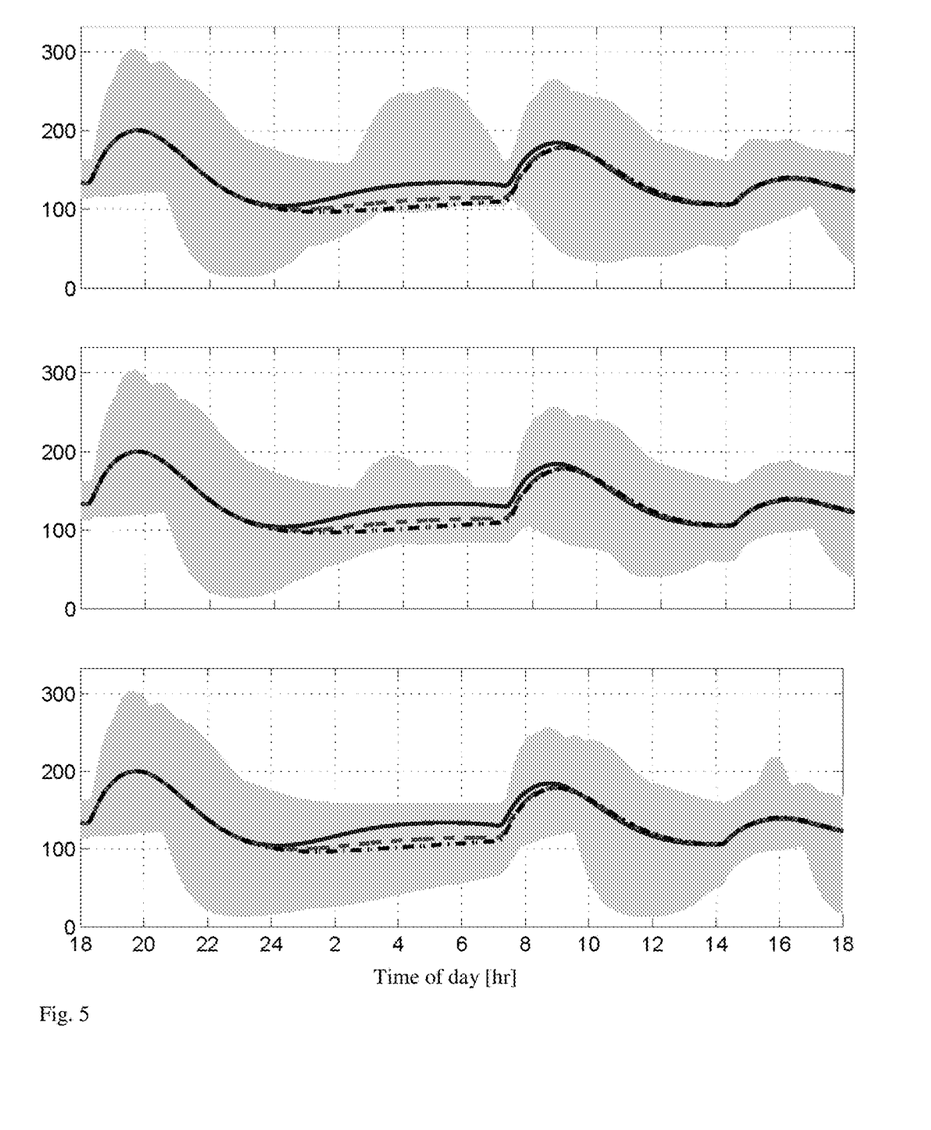
FIG. 5. Blood-glucose mean trajectories and min-max envelopes.

Plotted in FIG. 5 are the trajectories of mean blood-glucose values over all 100 in silico subjects. The three control strategies produce very similar mean responses until midnight and after 9 am, with the PZMPC, invariant-zone MPC and nighttime-basal strategies producing successively lower mean glucose responses during the night and early morning.

Also plotted in FIG. 5 are the min-max envelopes of the blood-glucose responses for the three contrasted control strategies. Again, before midnight and after about 9 am the envelopes are very similar. However, the PZMPC, invariant-zone MPC and nighttime-basal strategies result in significantly different nighttime envelope boundaries. Of particular interest for the purpose of increased safety margins is that with the PZMPC approach the nighttime lower-bound of the envelope spends much time near (partly above) 100 mg/dL.

Statistics on the average, over 100 in silico subjects, insulin delivery and blood-glucose values are tabulated in Table I. The summary conclusion is the same as that stated in Section IV-B for the typical subject response of FIG. 3.

The ratio of mean blood-glucose level achieved with invariant-zone MPC vs. the mean blood-glucose level achieved with PZMPC is less than unity for each in silico subject, both for the whole day and only nighttime. The ratio of total insulin delivery with invariant-zone MPC vs. the total insulin delivery with PZMPC is greater than unity for each in silico subject during the night, and greater than unity for all except one in silico subject for the whole day. The one exception is described in more detail in Section IV-D.

Figure 6:
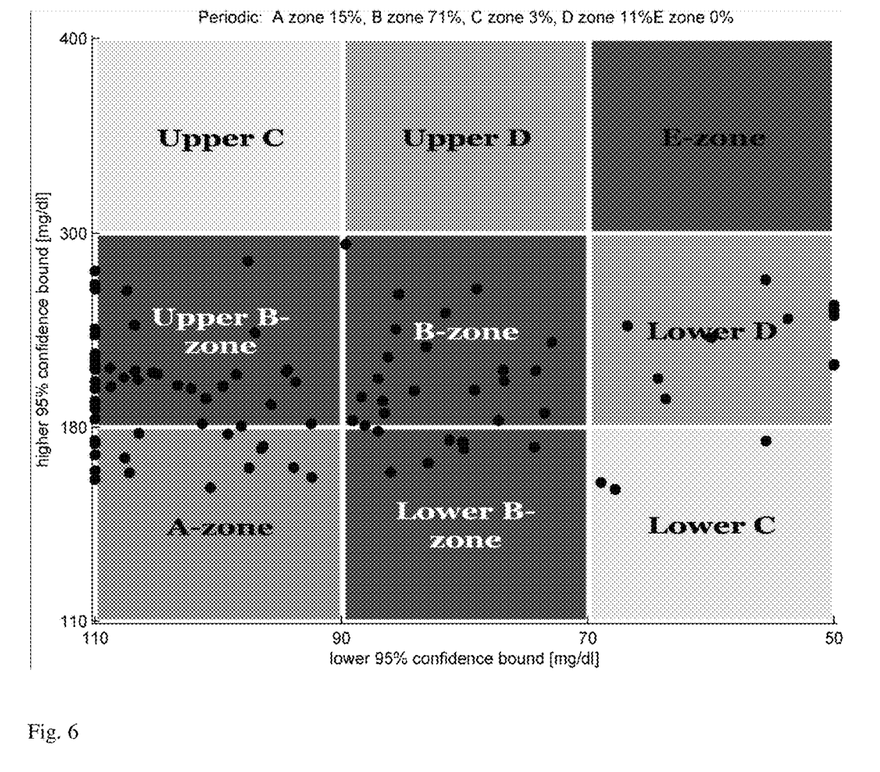
FIG. 6. CVGA plot for 100 in silico subjects and PZMPC.

The CVGA [16] results for the three compared control strategies are very similar because the strategies only differ for a few hours a day. The CVGA plot for the PZMPC case is depicted in FIG. 6, and the CVGA statistics for all three strategies are tabulated in Table II.

D. An Atypical Case

With one in silico subject the total amount of insulin over the whole day, when using PZMPC, exceeded the total amount of insulin delivered by the invariant-zone MPC strategy. The three control strategies' responses are plotted in FIG. 4. The blood-glucose responses are significantly different after about midnight, with very elevated blood glucose levels resulting from the use of PZMPC. The reason why PZMPC results in a higher total insulin delivery is due to the high input rates commanded from shortly before 5 am until 7 am, when the nighttime zone ([110,220] mg/dL) transitions to the daytime zone ([80,140] mg/dL).

The behavior is a statistical exception, but not surprising, and conforms to the response that can be expected from the PZMPC controller. One of the purposes of the Uni. Padova/UVa simulator is to facilitate the testing of glycemia controllers on virtual patients that have physiological parameters over a wide spectrum.

E. Other Scenarios

The disclosed PZMPC strategy was tested via simulations in other scenarios, and it demonstrated excellent responses to unannounced meals, severe hypoglycemia, and unannounced, self-administered insulin boluses.

V. CONCLUSION

An MPC strategy employing daily periodic blood-glucose target zones and daily periodic insulin input constraints is provided to safely operate glycemia controllers for prolonged, multi-day periods, including times that the subject is asleep. This control strategy is useful for the testing, verification and operation of an artificial pancreas for the treatment of T1DM. In silico testing confirmed that the strategy achieves the goal of reducing the threat of hypoglycemia during nighttime. More advanced periodic MPC schemes are also provided; for example, the inclusion of diurnal physiological time-dependence in the insulin-glucose dynamics, and the incorporation of time-dependent changes in subject behavior over a typical week.

REFERENCES

[1] H. Zisser, "Clinical hurdles and possible solutions in the implementation of closed-loop control in type 1 diabetes mellitus," J of Diabetes Science and Technology, vol. 5, pp. 1283-1286, September 2011.

[2] C. Cobelli, C. Dalla Man, G. Sparacino, L. Magni, S. De Nicolao, and B. P. Kovatchev, "Diabetes: Models, Signals and Control," IEEE Reviews in Biomedical Engineering, vol. 2, pp. 54-96, 2009.

[3] R. A. Harvey, Y. Wang, B. Grosman, M. W. Percival, W. Bevier, D. A. Finan, H. Zisser, D. E. Seborg, L. Jovanovic, F. J. Doyle III, and E. Dassau, "Quest for the Artificial Pancreas: Combining Technology with Treatment," IEEE Engineering in Medicine and Biology Magazine, vol. 29, no. 2, pp. 53-62, 2010.

[4] R. S. Parker, F. J. Doyle III, and N. A. Peppas, "A Model-Based Algorithm for Blood Glucose Control in Type 1 Diabetic Patients," IEEE Transactions on Biomedical Engineering, vol. 46, pp. 148-157, February 1999.

[5] K. van Heusden, E. Dassau, H. C. Zisser, D. E. Seborg, and F. J. Doyle III, "Control-Relevant Models for Glucose Control Using A Priori Patient Characteristics," IEEE Transactions on Biomedical Engineering, vol. 59, pp. 1839-1849, July 2012.

[6] B. Grosman, E. Dassau, H. C. Zisser, L. Jovanovic, and F. J. Doyle III, "Zone model predictive control: A strategy to minimize hyper- and hypoglycemic events," Journal of Diabetes Science and Technology, vol. 4, pp. 961-975, July 2010.

[7] L. Magni, D. M. Raimondo, C. Dalla Man, G. De Nicolao, B. Kovatchev, and C. Cobelli, "Model predictive control of glucose concentration in type 1 diabetic patients: An in silico trial," Biomedical Signal Processing and Control, vol. 4, no. 4, pp. 338-346, 2009.

[8] G. M. Steil, K. Rebrin, C. Darwin, F. Hariri, and M. F. Saad, "Feasibility of Automating Insulin Delivery for the Treatment of Type 1 Diabetes," Diabetes, vol. 55, pp. 3344-3350, December 2006.

[9] G. Marchetti, M. Barolo, L. Jovanovic, H. Zisser, and D. E. Seborg, "A feedforward-feedback glucose control strategy for type 1 diabetes mellitus," Journal of Process Control, vol. 18, pp. 149-162, February 2008.

[10] B. S. Leon, A. Y. Alanis, E. N. Sanchez, F. Ornelas-Tellez, and E. Ruiz-Velazquez, "Inverse optimal neural control of blood glucose level for type 1 diabetes mellitus patients," Journal of the Franklin Institute, vol. 349, pp. 1851-1870, June 2012.

[11] B. Grosman, E. Dassau, H. Zisser, L. Jovanovic, and F. J. Doyle III, "Multi-Zone-MPC: Clinical Inspired Control Algorithm for the Artificial Pancreas," in Proc. 18th IFAC World Congress, (Milan, Italy), pp. 7120-7125, August 2011.

[12] R. Hovorka, "Continuous glucose monitoring and closed-loop systems," Diabetic Medicine, vol. 23, pp. 1-12, January 2006.

[13] R. Gondhalekar, F. Oldewurtel, and C. N. Jones, "Least-restrictive robust MPC of constrained discrete-time periodic affine systems with application to building climate control," in Proc. 49th IEEE Conf. Decision & Control, (Atlanta, Ga., USA), pp. 5257-5263, December 2010.

[14] W. S. Levine, ed., The Control Handbook. CRC Press, 2 ed., 2011.

[15] B. P. Kovatchev, M. Breton, C. Dalla Man, and C. Cobelli, "In Silico Preclinical Trials: A Proof of Concept in Closed-Loop Control of Type 1 Diabetes," Journal of Diabetes Science and Technology, vol. 3, pp. 44-55, January 2009.

[16] L. Magni, D. M. Raimondo, C. Dalla Man, M. Breton, S. Patek, G. De Nicolao, C. Cobelli, and B. Kovatchev, "Evaluating the Efficacy of Closed-Loop Glucose Regulation via Control-Variability Grid Analysis," Journal of Diabetes Science and Technology, vol. 2, pp. 630-635, July 2008.

TABLE I

RATIO OF SUMMED INSULIN DELIVERY AND AVERAGE BLOOD-GLUCOSE LEVELS USING INVARIANT-ZONE MPC AND NIGHTTIME-BASAL VS. THOSE OF PZMPC. WHOLE DAY: 6 PM-6 PM. NIGHTTIME: 10 PM-5 AM.

Figure 3:
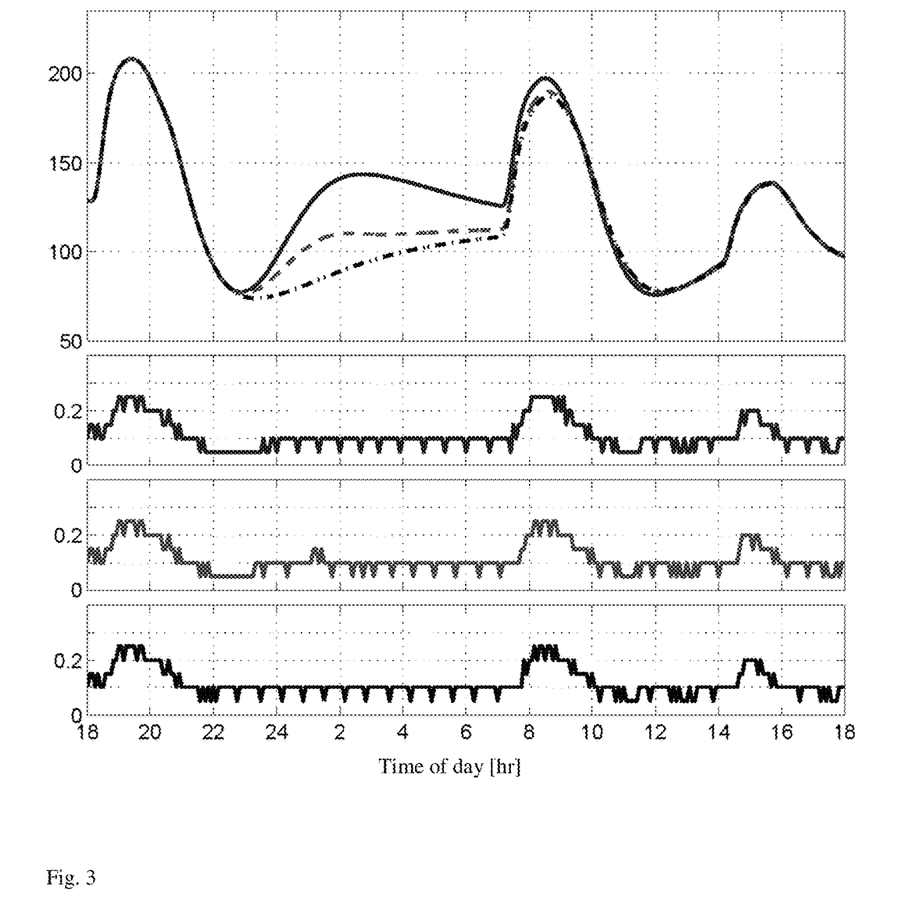
FIG. 3. Simulation result.
Figure 4:
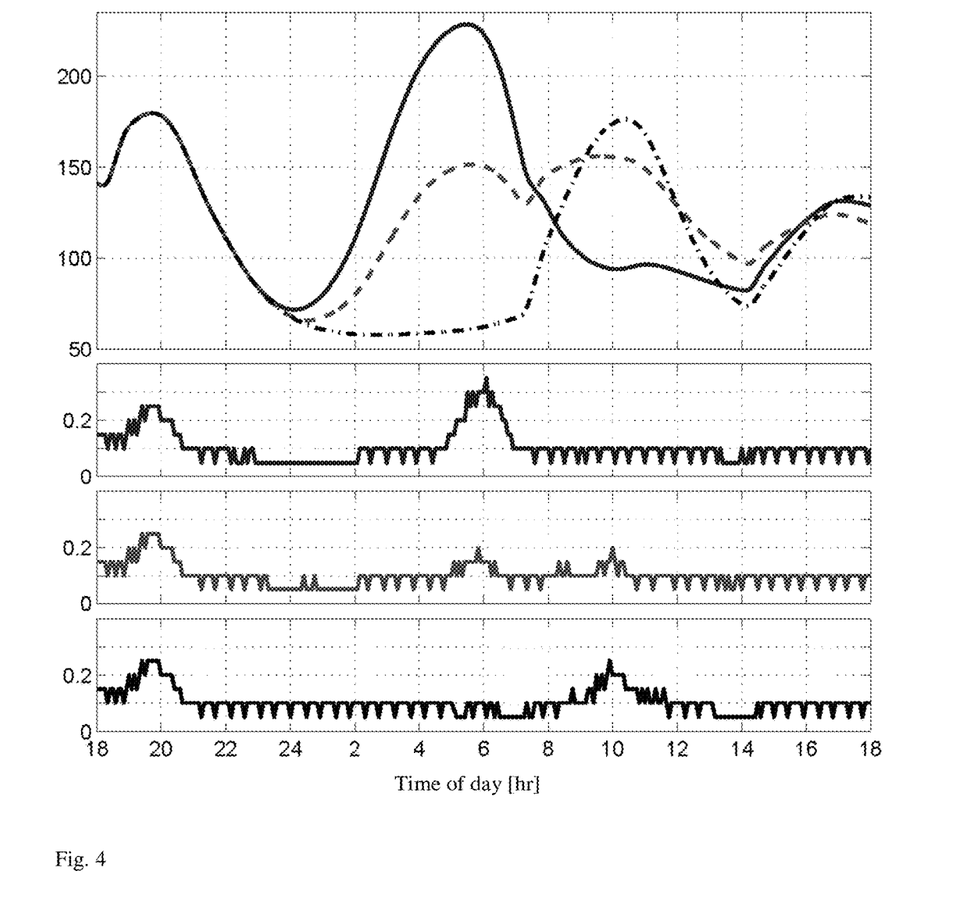
FIG. 4. Simulation result.

| | Insulin delivery | | Blood-glucose levels | |
|---|---|---|---|---|
| Control strategy | All day | Nighttime | All day | Nighttime |
| PZMPC | :=1 | :=1 | :=1 | :=1 |
| Subject of FIG. 3 | | | | |
| Invariant-zone MPC | 1.027 | 1.151 | 0.938 | 0.831 |
| Nighttime-basal | 1.047 | 1.262 | 0.905 | 0.730 |
| Subject of FIG. 4 | | | | |
| Invariant-zone MPC | 0.993 | 1.217 | 0.968 | 0.761 |
| Nighttime-basal | 1.019 | 1.685 | 0.825 | 0.537 |
| 100 subject mean | | | | |
| Invariant-zone MPC | 1.020 | 1.148 | 0.961 | 0.909 |
| Nighttime-basal | 1.027 | 1.207 | 0.946 | 0.868 |

TABLE II

CVGA STATISTICS FOR 100 IN SILICO SUBJECTS

| | CVGA zone inclusion [%] | | | | |
|---|---|---|---|---|---|
| Control strategy | A | B | C | D | E |
| PZMPC | 15 | 71 | 3 | 11 | 0 |
| Invariant-zone MPC | 13 | 73 | 2 | 12 | 0 |
| Nighttime-basal | 13 | 71 | 5 | 11 | 0 |

FIGURES

Figure 1:
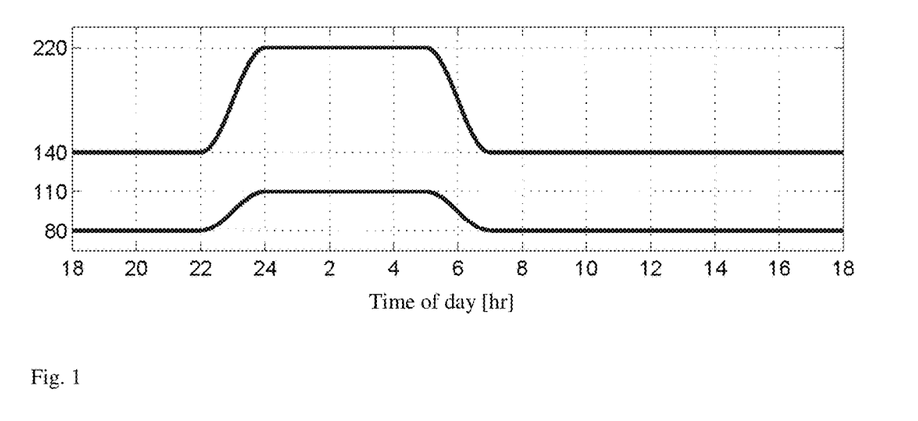
FIG. 1. Daily periodic blood-glucose target zone boundaries.

FIG. 1. Daily periodic blood-glucose ($y_{BG}$) target zone boundaries [mg/dL]. Daytime: 7 am-10 pm. Nighttime: 12 pm-5 am. Daytime zone: [80; 140] mg/dL. Nighttime zone: [110; 220] mg/dL. Smooth transition of two hour duration (5-7 am, 10-12 pm) based on cosine function.

Figure 2:
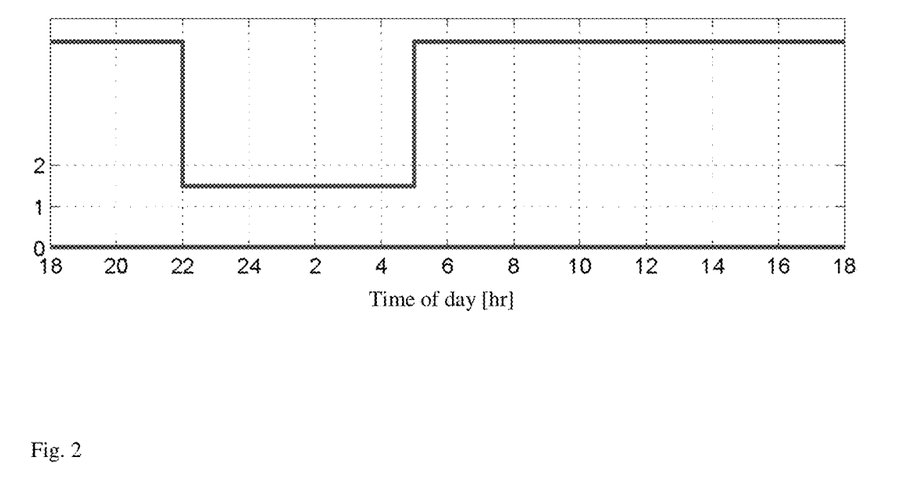
FIG. 2. Daily periodic constraints on the insulin input rate $u_{IN}$.

FIG. 2. Daily periodic constraints on the insulin input rate $u_{IN}$ [U/h]. Daytime: 5 am-10 pm. Nighttime: 10 pm-5 am. Daytime upper-bound is pump-maximum: Hardware dependent. Nighttime upper-bound is 1:5 $u_{basal}$: Subject-specific. Lower-bound is 0 [U/h] at all times.

FIG. 3. Simulation result. Top plot is blood-glucose [mg/dL]: PZMPC (blue, solid), invariant-zone MPC (red, dashed), nighttime-basal (black, dash-dotted). Lower three plots are insulin input rate [U/h]: PZMPC (blue, top), invariant-zone MPC (red, middle), nighttime-basal (black, bottom). This in silico subject results in trajectories with typical characteristics.

FIG. 4. Simulation result. Top plot is blood-glucose [mg/dL]: PZMPC (blue, solid), invariant-zone MPC (red, dashed), nighttime-basal (black, dash-dotted). Lower three plots are insulin input rate [U/h]: PZMPC (blue, top), invariant-zone MPC (red, middle), nighttime-basal (black, bottom). This in silico subject resulted in atypically large deviations between the contrasted control laws. PZMPC resulted in more total insulin delivery than invariant-zone MPC and nighttime-basal strategies.

FIG. 5. Blood-glucose ($y_{BG}$ [mg/dL]) mean trajectories and min-max envelopes over 100 in silico subjects. Mean trajectories identical on each subplot: PZMPC (blue, solid), invariant-zone MPC (red, dashed), nighttime-basal (black, dash-dotted). Envelopes: PZMPC (top), invariant-zone MPC (middle), nighttime-basal (bottom).

FIG. 6. CVGA plot for 100 in silico subjects and PZMPC (see also Table II).

VI. ALGORITHM—SUPPLEMENTAL DETAILS

This example describes a modification to our Zone MPC algorithm, and facilitates operating Zone MPC glycemia controllers in fully closed-loop mode for extended, multi-day periods of time. Operating glycemia controllers for extended periods of time is indispensable for the development, testing and verification of an artificial pancreas that is fully automated and requires no specialist supervision.

Controller Overview: Glucose Feedback for Glycemia Control

Figure 7:
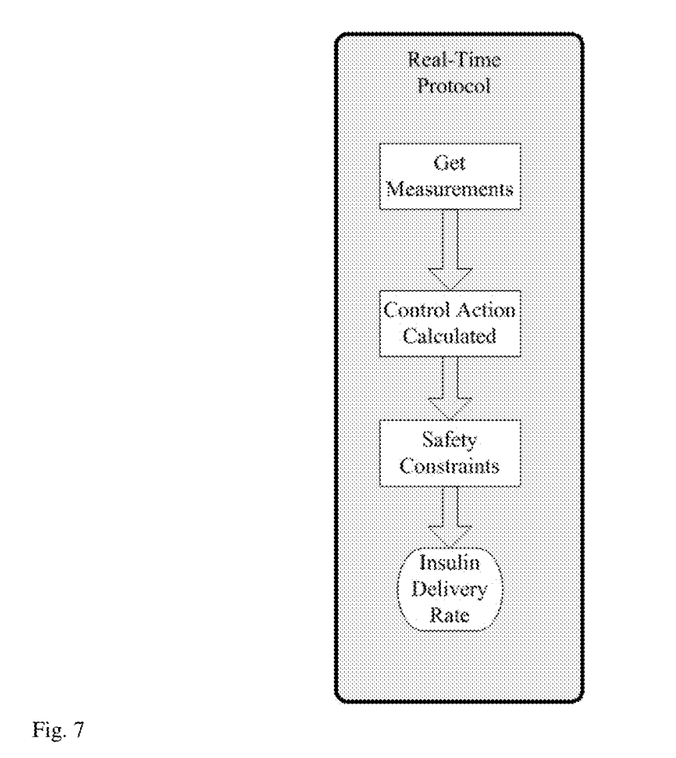
FIG. 7. Process flow diagram of the real-time control protocol.

The control strategy employed is a feedback-control strategy, where measurements of blood glucose values are used by the controller in order to determine a value of the insulin input that is applied to the subject. An outline of the real-time control protocol is shown in FIG. 7. This example refers in its entirety to the operation "Control Action Calculated".

The control strategy is formulated in a discrete-time setting, with a sample period $T_s$=5 min. The integer variable k denotes the current discrete-time step index, such that at discrete-time step k the actual continuous-time t is given by t=$kT_s$ since controller initialization.

Model Predictive Control (MPC)

The control algorithm is a so-called Model Predictive Control (MPC) algorithm. MPC employs an explicit model of the process to be controlled when optimizing the input. Specifically, MPC controllers for glycemia control use a model of a human's T1DM glucose-insulin dynamics to predict the evolution of the blood glucose values over a so-called prediction horizon of P controller steps, and optimize a predicted insulin input trajectory in order to optimize a specified cost objective that penalizes unsafe glycemic values and also insulin usage. Thus at each step k the MPC controller determines an optimal predicted insulin input trajectory into the future. However, only the first insulin input of the optimal trajectory is applied to the subject, and at the next step k+1 the optimization process is repeated.

MPC is based on real-time numerical optimization, and this allows for a large degree of flexibility when defining the control objective. For example, constraints can be incorporated explicitly into the optimization routine. In glycemia control, constraints on the input ensure that insulin delivery rates are constrained between prescribed minimum and maximum values.

Zone MPC

Another mechanism of exploiting the flexibility of MPC is to consider Zone MPC. In Zone MPC for glycemia control the controller strives to maintain a blood glucose level that is within a safe zone, rather than controlling the blood glucose level to a specific set point. Zone MPC is applied when a specific set point value of a controlled variable (CV) is of low relevance compared to a zone that is defined by upper and lower boundaries. Moreover, in the presence of glucose measurement noise and plant/model mismatches there is no practical value using a fixed set point for closed-loop blood glucose regulation. The Zone MPC strategy of this work is implemented by defining upper and lower bounds (see FIG. 8) as soft constraints and optimizing the insulin input computation by penalizing, by means of an appropriate cost function, the deviations of predicted blood glucose levels beyond the zone.

Figure 8:
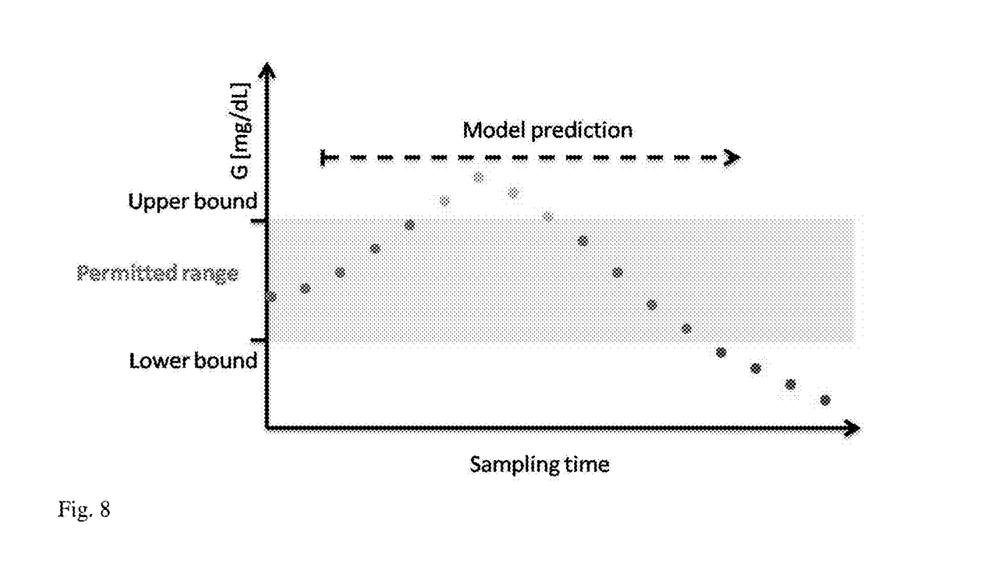
FIG. 8. Illustration of Zone MPC in the context of diabetes.
Figure 9:
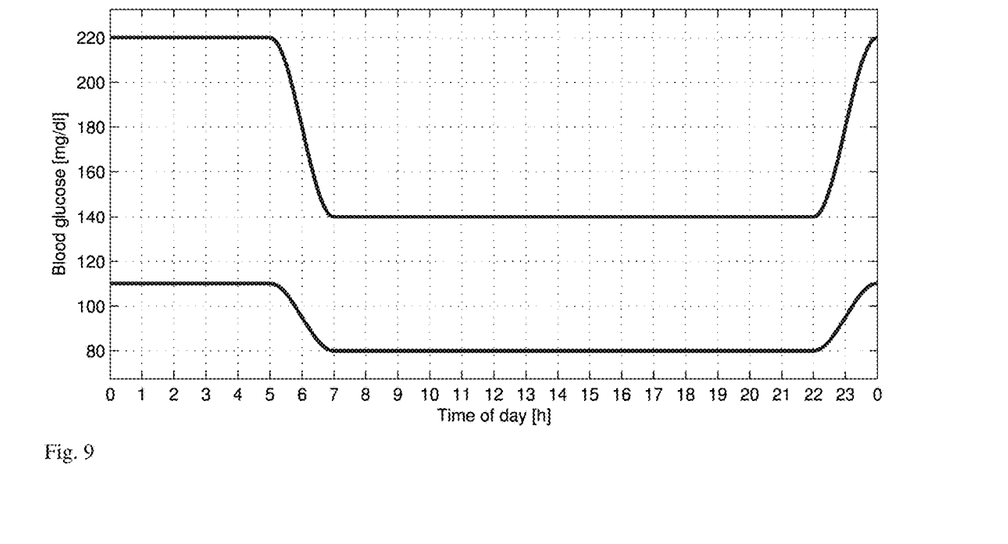
FIG. 9. Upper and lower boundary of periodic safe glucose zone: Nominal settings.

FIG. 8 illustrates the three zones defined in the Zone MPC, from top to bottom: Undesirably high glycemia value zone, controller target zone, and undesirably low glycemia value zone. The green dots in FIG. 8 indicate predicted glycemic values that are in the desired range. The upper zone represents undesirably high predicted glycemic values that are represented by orange dots. The lower zone represents undesirably low predicted glycemic values, symbolized by red dots. The zone below the lower bound represents either a hypoglycemic zone, or a pre-hypoglycemic protective area that is a low alarm zone.

Periodic Zones

The first of three significant changes from IDE G110093 is that Zone MPC is performed employing periodically time-dependent zones, where the periodic time-dependence is with respect to the time of day. The purpose of this is to let the controller maintain safe glucose zones during the night that are different from the safe glucose zones maintained during the day, and to facilitate a smooth transition between the night and day zones. Specifically, it is desired that during the night a higher safe zone be maintained than during the day, in order to reduce the likelihood of (controller induced) hypoglycemic events during sleep. A smooth transition between night and day zones is achieved by smoothly shifting the zone boundaries according to a cosine function.

Periodic Input Constraints

The second of three significant changes from IDE G110093 is that the online optimization of the insulin input, performed as part of the Zone MPC routine, is performed with respect to hard constraints that are periodically time-dependent. The periodic time-dependence is again based on the time of day. Under the disclosed scheme the upper limit of insulin input during the day is higher than the upper limit imposed during the night. Specifically, during the day the maximum insulin input is the maximum insulin amount deliverable by the pump, and is hardware dependent. This is the same as in the Zone MPC algorithm described in the aforementioned references. However, during the night the maximum insulin input is a small amount higher than the basal infusion rate, and is patient dependent. The amount by which the upper limit is higher than a patient's basal rate is a design parameter (θ, see Table S2). The purpose of having such time-dependent insulin input constraints is again to reduce the possibility of over-delivery of insulin while a patient is asleep. While appropriate choices of the safe zone definitions during the night and day should result in a controller giving near-basal insulin inputs, the night-time input constraint, enforced explicitly within the input optimization, acts as a further safety mechanism, preventing the administration of excessive insulin.

MPC is a State-Feedback Strategy

The third of three significant changes from IDE G110093 is an improved mechanism of computing the state-estimator gain. MPC is a state-feedback control strategy. This means that at each time step k that the controller is invoked, the controller's internal model must be initialized to the most appropriate state, such that glucose predictions correspond as closely as possible to reality. In the case of glycemia control an appropriate state is not directly measurable. Therefore a state-estimator is employed to estimate the most appropriate state from the available blood glucose measurements.

The state-estimator employed is a linear-estimator (sometimes referred to as a Luenberger-observer) and has a gain as a tuning parameter. There are various ways a suitable gain can be computed, and in this supplement a change to the method of gain computation is described. This method brings the gain-computation in-line with modern system-theoretic methodologies.

Periodic-Zone MPC

Overall the disclosed control mechanism is referred to as Periodic-Zone Model Predictive Control (PZMPC).

PZMPC Algorithm Parameters

The variables and fixed parameters of the PZMPC algorithm are listed in Table S1. Changes from IDE G110093 are summarized in the right-most column

TABLE S1

| | | | Notation guide and parameter list for Zone MPC. | |
|---|---|---|---|---|
| Symbol | Value | Unit | Interpretation | Change status |
| k | — | — | Sample index | No change |
| τ(k) | — | min | Time of day corresponding to the discrete time index k. | New. Employed to get time from step number in Eq. (7). |
| $T_s$ | 5 | min | Sampling period | No change |
| $I_D(k)$ | — | U/h | Insulin delivery rate at sample k | No change |
| basal(k) | [P.S.] | U/h | Basal insulin delivery rate at sample k | No change |
| TDI | [P.S.] | U | Total Daily Insulin | No change |
| $I_D'(k)$ | — | U/h | Deviation insulin delivery rate at sample k [equal to $I_D$-basal(k))] | No change |
| G (k) | — | mg/dL | CGM measurement at sample k | No change |
| G'(k) | — | mg/dL | Deviation of G(k) from 110 mg/dL | No change |
| $I_M(k)$ | — | U/h | Mapped insulin delivery rate at sample k | No change |
| C | $1.225 \cdot 10^{-6}$ | h | Conversion factor depends on the unit of the input. | No change |
| M | 5 | unitless | Control horizon: Number of predicted insulin delivery rates optimized by MPC routine | No change |
| P | 9 | unitless | Prediction horizon: Length of predicted blood glucose trajectory used in optimization by MPC routine | Shortened from 100 (45 min) due to lack of prediction quality beyond 9 steps. |
| Q | 1 | $\left(\frac{dL}{mg}\right)^2$ | Weighting factor for the glucose term in the cost function | No change |
| J(k) | — | unitless | MPC cost function | No change |
| $G^{zone}$ | — | mg/dL | Model predictions of glucose optimized in the MPC that are zero when within the glucose zone and non-zero when outside the glucose zone | No change |
| $I_{D0}'(k)$ | [0 0 0 0 0] | U/h | Initial guess for $I_D'(k)$ used in the optimization of the cost function | No change |
| $K_i$ | 1800/TDI | $\frac{mg \cdot U}{dL}$ | Individual gain based on correction factor using 1800 rule. | No change |
| Max_f | 500 | unitless | Maximum number of function evaluations allowed in the optimization of the cost function | No change |
| Max_i | 400 | unitless | Maximum number of iterations allowed in the optimization of the cost function | No change |
| Term_cost | $10^{-6}$ | unitless | Threshold for the termination of the cost function | No change |
| Term_tol | $10^{-6}$ | unitless | Threshold for the termination tolerance in the cost function | No change |
| $G_{ZL}(t)$ | — | mg/dL | Lower limit of the safe glucose zone as a function of the time of day t in minutes. | Formerly fixed at 80. Now periodically time-dependent according to Eq. (4). |

TABLE S1-continued

Notation guide and parameter list for Zone MPC.

| Symbol | Value | Unit | Interpretation | Change status |
|---|---|---|---|---|
| $G_{ZH}(t)$ | — | mg/dL | Upper limit of the safe glucose zone as a function of the time of day t in minutes. | Formerly fixed at 140. Now periodically time-dependent according to Eq. (3). |
| $I_H(t)$ | — | U/h | Upper-bound on the insulin infusion rate $I_D'$ based on the time of day t in minutes. | New. See Eq. (5). |
| $F_s$ | 1.5 | unitless | Safety factor to limit controller aggressiveness. A value of one suggest perfect estimation of the subject's correction factor based on the 1800 rule, any value greater than one provides a more conservative control which will help in avoiding hypoglycemia | Formerly in the range 1.25-2.0. New value is fixed because the Q:R ratio is a more effective tuning variable than $F_s$. |
| $\hat{Q}$ | 1000 | unitless | State estimator error weighting matrix | New. See Eq. (6). |
| $\hat{R}$ | 1 | unitless | State estimator weighting matrix | New. See Eq. (6). |
| $V_{UD}$ | 140 | mg/dL | Daytime safe glucose zone upper bound. | New. Same as former fixed $G_{ZH}$. See Eq. (3). |
| $V_{LD}$ | 80 | mg/dL | Daytime safe glucose zone lower bound. | New. Same as former fixed $G_{ZL}$. See Eq. (4). |
| Ipump | — | U/h | Maximum insulin infusion rate achievable by the particular pump employed: Usually 120 | New. See Eq. (5). |

P.S. = patient specific.

The adjustable parameters used in the PZMPC algorithm are listed in Table S2. These parameters are adjustable in the sense that they may be adjusted, within the ranges listed in Table S2, between clinical trials. However, they remain constant throughout any one trial. Changes from IDE G110093 are summarized in the right-most column

TABLE S2

Notation guide for the adjustable parameters in the Zone MPC.

| Symbol | Min Value | Nominal Value | Max Value | Unit | Interpretation | Change status |
|---|---|---|---|---|---|---|
| R | 12 | 15 | 50 | $\left(\frac{h}{u}\right)^2$ | Weighting factor for the insulin term in the cost function | Formerly fixed at 50. |
| $T_{Z1}$ | 240 | 300 | 360 | min | End of nighttime, start of transition to daytime. | New. See Eqs. (3), (4), (5). |
| $T_{Z2}$ | 360 | 420 | 480 | min | Start of daytime, end of transition from nighttime. | New. See Eqs. (3), (4). |
| $T_{Z3}$ | 1260 | 1320 | 1380 | min | End of daytime, start of transition to nighttime. | New. See Eqs. (3), (4), (5). |
| $T_{Z4}$ | 1380 | 1440 | 1500 | min | Start of nighttime, end of transition from daytime. | New. See Eqs. (3), (4). |
| $V_{UN}$ | 140 | 220 | 280 | mg/dL | Nighttime safe glucose zone upper bound. | New. See Eq. (3). |
| $V_{LN}$ | 80 | 110 | 140 | mg/dL | Nighttime safe glucose zone lower bound. | New. See Eq. (4). |
| θ | 0 | 0.5 | 1 | unitless | Multiplier on basal infusion rate, employed as upper-bound during nighttime. | New. See Eq. (5). |

The unit of minutes for $T_{Z1}$, $T_{Z2}$, $T_{Z3}$, and $T_{Z4}$ refers to the number of minutes since midnight. Note that the time parameters must be strictly monotonically increasing, i.e., $T_{Z1} < T_{Z2} < T_{Z3} < T_{Z4}$. Note further that a time parameter exceeding one day (24 h·60 min/h=1440 min) is allowed. However, it must hold that $T_{Z4} - T_{Z1} < 1440$ min, i.e., the start of nighttime must be strictly less than one day after the end of nighttime.

Detailed Description of Periodic-Zone MPC: Model Implementation

We consider the following transfer function from insulin rate to glucose deviation:

$$Y(z) = \frac{G'(z)}{I'_D(z)} = F_s K_i C \frac{z^{-3}}{(1 - 0.98z^{-1})(1 - 0965z^{-1})^2}.$$

Converting the above to a state space model yields $$x[k+1] = Ax[k] + BI'_D[k] \quad (1)$$

$$G'[k] = Cx[k] + DI'_D[k] \quad (2)$$

where, $$x[k] = \begin{bmatrix} x_1[k] \\ x_2[k] \\ x_3[k] \end{bmatrix}$$

$$A = \begin{bmatrix} 2.91 & -2.8226 & 0.9126 \\ 1 & 0 & 0 \\ 0 & 1 & 0 \end{bmatrix}$$

$$B = \begin{bmatrix} 1 \\ 0 \\ 0 \end{bmatrix}$$

$$C = [0 \ 0 \ -F_s K_i C]$$

$$D = 0$$

and:
G' is the glucose concentration output (G) deviation variable (mg/dL), i.e., G':=G−110 mg/dL,
$I'_D$ is the insulin infusion rate input ($I_D$) deviation variable (U/h), i.e., $I'_D$:=$I_D$−basal U/h,
C is the conversion factor and depends on the unit of the insulin infusion rate, i.e., $1.225 \cdot 10^4$ for the insulin infusion rate in (U/h),
$F_S$ is a safety factor,
$K_i$ is an individualized gain based on the correction factor using the 1800 rule:

$$K_i := \frac{1800}{\text{Total Daily Insulin}} \left[ \frac{\text{mg} \cdot U}{\text{dL}} \right].$$

Changes made to the model implementation from IDE G110093 are tabulated below. In summary, the state-space realization of the transfer function was changed from observer canonical form to the controller canonical form.

| Variable | Previous value | Current value |
|---|---|---|
| x[k] | $\begin{bmatrix} G'[k] \\ I_M[k] \\ I_M[k-1] \end{bmatrix}$ | $\begin{bmatrix} x_1[k] \\ x_2[k] \\ x_3[k] \end{bmatrix}$ |

-continued

| Variable | Previous value | Current value |
|---|---|---|
| A | $\begin{bmatrix} 0.98 & -F_s K_i C & 0 \\ 0 & 1.9300 & -0.9312 \\ 0 & 1 & 0 \end{bmatrix}$ | $\begin{bmatrix} 2.91 & -2.8226 & 0.9126 \\ 1 & 0 & 0 \\ 0 & 1 & 0 \end{bmatrix}$ |
| B | $\begin{bmatrix} 0 \\ 1 \\ 0 \end{bmatrix}$ | $\begin{bmatrix} 1 \\ 0 \\ 0 \end{bmatrix}$ |
| C | [1 0 0] | [0 0 $-F_s K_i C$] |

Periodic Safe Glucose Zone Definition

The periodic safe glucose zone definitions are as follows:

$$G_{ZH}(t) := \begin{cases} \frac{V_{UN} - V_{UD}}{2} \cos\left(\pi \frac{t - T_{Z1}}{T_{Z2} - T_{Z1}}\right) + \frac{V_{UD} + V_{UN}}{2} & \text{if } T_{Z1} \leq t < T_{Z2} \\ V_{UD} & \text{if } T_{Z2} \leq t < T_{Z3} \\ \frac{V_{UD} - V_{UN}}{2} \cos\left(\pi \frac{t - T_{Z3}}{T_{Z4} - T_{Z3}}\right) + \frac{V_{UD} + V_{UN}}{2} & \text{if } T_{Z3} \leq t < T_{Z4} \\ V_{UN} & \text{otherwise} \end{cases} \quad (3)$$

$$G_{ZL}(t) := \begin{cases} \frac{V_{LN} - V_{LD}}{2} \cos\left(\pi \frac{t - T_{Z1}}{T_{Z2} - T_{Z1}}\right) + \frac{V_{LD} + V_{LN}}{2} & \text{if } T_{Z1} \leq t < T_{Z2} \\ V_{LD} & \text{if } T_{Z2} \leq t < T_{Z3} \\ \frac{V_{LD} - V_{LN}}{2} \cos\left(\pi \frac{t - T_{Z3}}{T_{Z4} - T_{Z3}}\right) + \frac{V_{LD} + V_{LN}}{2} & \text{if } T_{Z3} \leq t < T_{Z4} \\ V_{LN} & \text{otherwise} \end{cases} \quad (4)$$

The specific example of zone when employing the nominal settings tabulated in Table S2 is plotted in FIG. 3S.

The input constraint is as follows:

$$I_H(t) := \begin{cases} I_{pump} & \text{if } T_{Z1} \leq t \leq T_{Z3} \\ \theta \cdot \text{basal} & \text{otherwise} \end{cases} \quad (5)$$

Note that the change in night and day mode for the insulin input constraint occurs at the start of the transition of the safe glucose zone from night to/from day mode.

Note further that the variable $I'_D$ denotes the offset of the actual infusion rate to the basal infusion rate. Thus, to enforce that the actual infusion rate is constrained to be, e.g., 1.5 times the basal infusion rate, one must employ θ=0.5.

State Estimator Gain Computation

Let $\tilde{x}(k) \in \mathbb{R}^3$ denote the state of the state-estimator. Then, the estimator state is updated according to $$\tilde{x}(k+1) = A\tilde{x}(k) + BI'_D(k) + Le(k)$$

where $L \in \mathbb{R}^3$ denotes the estimator gain, and $e(k):=y(k)-C\tilde{x}(k) \in \mathbb{R}$ denotes the estimation error.

The gain L must be chosen such that $\rho(A-LC)<1$, where $\rho(\ )$ denotes the spectral radius. A straightforward method to determine a suitable L is by solving a Riccati equation, as follows:

Let $\hat{A} := A^T$, $\hat{B} := -C^T$, where $A^T$ is the transpose of A. Let $Q \in \mathbb{R}^3$ and $R \in \mathbb{R}$ be design parameters that must be positive semi-definite, and positive definite, respectively. Let P satisfy the discrete-time Riccati equation $$P = \hat{A}^T P \hat{A} + \hat{Q} - \hat{A}^T P \hat{B}(\hat{R} + \hat{B}^T P \hat{B})^{-1} \hat{B}^T P \hat{A}. \quad (6)$$

Finally:

$$L := K^T$$

$$K := -(\hat{R} + \hat{B}^T P \hat{B})^{-1} \hat{B}^T P \hat{A}.$$

The following is a sample calculation of state estimator gain. Subject 1 of the UVA Padova has the following:

$$A = \begin{bmatrix} 2.91 & -2.8226 & 0.9126 \\ 1 & 0 & 0 \\ 0 & 1 & 0 \end{bmatrix}$$

$$C = \begin{bmatrix} 0 & 0 & -8.8474 \cdot 10^{-5} \end{bmatrix}.$$

Let:

$$\hat{Q} = \begin{bmatrix} 1000 & 0 & 0 \\ 0 & 1000 & 0 \\ 0 & 0 & 1000 \end{bmatrix}$$

$$\hat{R} = 1.$$

The Then, solve for P in the Riccati equation, $$P = \begin{bmatrix} 7.7609 & 6.7129 & 5.7185 \\ 6.7129 & 5.8545 & 5.0345 \\ 5.7185 & 5.0345 & 4.3769 \end{bmatrix} \cdot 10^7.$$

L is given as $$L = \begin{bmatrix} -4233.7 \\ -3768.3 \\ -3317.6 \end{bmatrix}$$

We verify the convergence of the state estimator by making sure that $\rho(A-LC) < 1$.

$$A - LC = \begin{bmatrix} 2.91 & -2.8226 & 0.5380 \\ 1 & 0 & -0.3334 \\ 0 & 1 & -0.2935 \end{bmatrix}$$

The three Eigenvalues are of A−LC are:

$$\lambda_1 = 0.8954 + 0.1466i$$

$$\lambda_2 = 0.8954 - 0.1466i$$

$$\lambda_3 = 0.8257.$$

It holds that $|\lambda_1| = |\lambda_2| = 0.9073$ and $|\lambda_3| = 0.8257$. Thus $\rho(A-LC) = 0.9073 < 1$ and we conclude that the determined value of L is suitable.

Changes made to the model implementation from IDE G110093 are tabulated below. In summary, the feedback gain is changed because the state estimator is changed from the ARX state estimator to the Luenberger state estimator.

| Variable | Previous value | Current value |
|---|---|---|
| L | $\begin{bmatrix} 1 \\ 0 \\ 0 \end{bmatrix}$ | $\begin{bmatrix} -4233 \\ -3768 \\ -3318 \end{bmatrix}$ |

PZMPC Law

The Zone MPC cost function $J(I'_D)$ used in the present work is defined as $$J(I'_D) = Q \cdot \sum_{j=1}^{P} \|G^{zone}(k+j)\|^2 + R \cdot \sum_{j=0}^{M-1} \|I'_D(k+j)\|^2$$

where Q and R are constant optimization weights on the predicted outputs and the future proposed inputs, respectively.

The zone-cost function is defined as follows:

$$G^{zone}(k+j) = \begin{cases} G(k+j) - G_{ZH}(\tau(k+j)) & \text{if } G(k+j) > G_{ZH}(\tau(k+j)) \\ G_{ZL}(\tau(k+j)) - G(k+j) & \text{if } G(k+j) < G_{ZL}(\tau(k+j)) \\ 0 & \text{otherwise} \end{cases} \quad (7)$$

In PZMPC the cost function $J(I'_D)$ is minimized subject to input constraints $$-\text{basal}(k+j) \leq I'_D(k+j) \leq I_H(t) \forall j = 1, \ldots, M-1$$

and furthermore subject to the prediction dynamics described in Eqs. (1) and (2).

Optimization Algorithm

MATLAB's function 'fmincon.m' ("trust-region-reflective" algorithm) is used to solve the optimization problem (i.e., the minimization of the cost function $J(I'_D)$). The following parameters are used for each optimization:

Initial guess for the insulin delivery rates, $I'_D(0)$, is the null vector, $0 \in \mathbb{R}^M$ e.g., if M=5 the initial guess for each optimization is $I'_D = [0\ 0\ 0\ 0\ 0]$. This implies that the initial guess is equivalent to the basal rate.

Maximum number of function evaluations allowed is Max_f=100M, where M is control horizon.

Maximum number of iterations is Max_i=400, which is fixed.

Termination on the cost function values Term_cost=$10^{-6}$, which is fixed.

Termination tolerance Term_tol on the manipulated variables $I'_D$ is $10^{-6}$.

Real-Time Control Algorithm Implementation

Once the controller is initialized and switched on, real-time calculations take place every five minutes, corresponding to the sample-period of the glucose sensor. Initialization corresponds to gathering enough information about glucose measurements and insulin delivery rates in order to determine a reliable state estimate to initialize the prediction.

Controller Parameters

Although the values of parameters M and P have significant effects on the controller performance, and are normally used to tune an MPC based controller, they can be heuristically tuned based on knowledge of the system. We use the nominal values of M=5 and P=9, which have been heuristically tuned.

The ratio of the output error weighting matrix (Q) and the input change weighting matrix (R) may be varied between:

$$12 \le \frac{R}{Q} \le 50.$$

We use the nominal value of $$\frac{R}{Q} = 15.$$

For the state estimator, the larger $\hat{Q}$ matrix resulted in faster convergence of the state estimate. However, an excessive value, e.g., $\hat{Q}=10000\cdot I$, resulted in instability of two subjects (subject 52 and 94), possibly due to the subject/model mismatch that is exacerbated by the high estimator. Thus, a useful value of $\hat{Q}$ matrix is determined to be between $1000\cdot I$ and $5000\cdot I$.

What is claimed is:

1. A controller for an artificial pancreas (AP) that automatically directs the delivery of insulin with real-time optimization to maintain blood glucose concentrations of a patient with type 1 diabetes mellitus (T1DM) the controller comprising and operated according to a periodic zone model predictive control (PZMPC) algorithm that continuously modulates control objective periodically based on a model of a human's insulin response to regulate blood glucose levels to time-dependent output target zones and to smoothly transition target zone boundaries, wherein the control objective is formulated based on blood-glucose levels controlled with respect to inclusion within a safety-set, rather than to track a singular set-point, wherein the smooth transition is achieved by smoothly shifting the target zone boundaries according to a cosine function, wherein the controller is operably connected to an insulin pump, and the controller directs delivery of insulin by the pump according to the algorithm.

2. A method comprising directing insulin delivery using the controller of claim 1 to automatically direct the delivery of insulin with real-time optimization to maintain blood glucose concentrations of a patient with type 1 diabetes mellitus (T1DM), wherein the control objective is modulated periodically based on the model to regulate the blood glucose levels to the time-dependent output target zones and to smoothly transition the target zone boundaries.

3. The method of claim 2 wherein the target zones comprise a euglycemic zone during the day and an elevated glycemic zone at night.

4. The method of claim 3 further comprising the step of delivering the insulin to the person.

5. The method of claim 2 wherein input constraints enforced by the controller are lower during the night than during the day, wherein elevated blood glucose levels are permitted during the night, and the maximum amount of insulin deliverable by the artificial pancreas device while the patient is asleep is reduced, and risk of controller induced hypoglycemia during periods of sleep is thus reduced.

6. The method of claim 5 further comprising the step of delivering the insulin to the person.

7. The method of claim 2 further comprising the step of delivering the insulin to the person.

8. The controller of claim 1 wherein the target zones comprise a euglycemic zone during the day and an elevated glycemic zone at night.

9. The controller of claim 1 wherein input constraints enforced by the controller are lower during the night than during the day, wherein elevated blood glucose levels are permitted during the night, and the maximum amount of insulin deliverable by the artificial pancreas device while the patient is asleep is reduced, and risk of controller induced hypoglycemia during periods of sleep is thus reduced.

* * * * *